United States Patent [19]

Loh et al.

[11] 4,361,553

[45] Nov. 30, 1982

[54] THERAPEUTIC USES OF DYNORPHIN

[75] Inventors: Horace H. Loh; Nancy M. Lee, both of San Francisco, Calif.

[73] Assignee: Regents of the University of California, Berkeley, Calif.

[21] Appl. No.: 264,830

[22] Filed: May 18, 1981

[51] Int. Cl.³ ............................................. A61K 37/00
[52] U.S. Cl. .................................................... 424/177
[58] Field of Search ........................................ 424/177

[56] References Cited

PUBLICATIONS

Way et al., *J. Pharmac, Exp. Ther.,* 167, pp. 1–8 (1969).
Tulunay et al., *J. Pharm. Exp. Ther.,* 190, pp. 395–400 (1974).
Litchfield et al., *J. Pharmacol. Exap. Ther.,* 96:99–113 (1949).
D'Amour et al., *J. Pharmac. Exp. Ther.,* 72, pp. 74–79 (1941).
Goldstein et al., *Proc. Natl. Acad. Sci. USA,* vol. 76, No. 12, pp. 6666–6670 (1979).
Herman et al., *Life Sciences,* vol. 27, pp. 883–892 (1980).
Friedman et al., "Dynorphin: A Possible Modulatory Peptide on Morphine or β-Endorphin Analgesia in Mouse", *Europ. J. Pharmacology* (in press).

*Primary Examiner*—Delbert R. Phillips
*Attorney, Agent, or Firm*—Majestic, Gallagher, Parsons & Siebert

[57] ABSTRACT

A therapeutic method of using dynorphin comprises administering dynorphin to a host tolerant to narcotic analgesics. Practice of the therapeutic method provides that lower doses of a narcotic analgesic may be used, such as for patients requiring chronic treatment with narcotics to ease pain, and for treatment of narcotics addicts.

11 Claims, No Drawings

THERAPEUTIC USES OF DYNORPHIN

The invention described herein was made in the course of work under a grant or award from the Department of Health and Human Services.

DESCRIPTION

Background of the Invention

1. Field of the Invention

The present invention generally relates to dynorphin, and more particularly to therapeutic uses of dynorphin for hosts tolerant to narcotic analgesics, such as opiate alkaloids.

2. Description of the Prior Art

One of the pituitary peptides to be recently discovered contains 17 amino acids and is generally referred to as dynorphin. Dynorphin has been discovered to have potent agonist properties in guinea pig ileum and mouse vas deferens. The sequence of the first 13 peptides have been determined, and dynorphin-(1–13) has been synthesized. The synthetic product has been found to be as potent in bioassays as the naturally occurring peptide, but was shown to be relatively weak in producing analgesia in studies with mice.

It has been recently reported that dynorphin-(1–13), but not the shorter fragment, dynorphin-(1–9), has significant effects on opiate and $\beta$-endorphin-induced analgesia in naive animals. The studies have suggested that dynorphin-(1–13) may interact with other analgesic opioids. Thus, it has been recently shown that dynorphin-(1–13) appears to interact with morphine to significantly attenuate, or inhibit, the analgesia produced by morphine in naive animals.

To date, dynorphin, and particularly dynorphin-(1–13), have been of interest in research laboratories, but have not found commercial applications.

SUMMARY OF THE INVENTION

It has been surprisingly discovered that dynorphin, and particularly dynorphin-(1–13), has an opposite effect in hosts tolerant to narcotic analgesics than the effect which has been observed in naive animals. Thus, instead of inhibiting morphine or $\beta$-endorphin-induced analgesia, dynorphin-(1–13) has been found to potentiate the analgesic effect in tolerant hosts.

Accordingly, in one aspect of the present invention, a therapeutic method of using dynorphin comprises administering a dose of dynorphin to a host tolerant to a narcotic analgesic. Practice of the therapeutic method in accordance with the present invention provides that lower doses of a narcotic analgesic, for example an opiate alkaloid such as morphine, may be used for patients requiring chronic treatment with narcotics to ease pain, such as terminal cancer patients, or that lower doses of a narcotic such as methadone may be used in treating narcotics addicts.

As a consequence, the various, known side effects, such as respiratory depression and constipation, which result from chronic treatment with high doses of narcotics, can be lessened.

Best Mode of Practicing the Invention

The present invention is useful with substantially all narcotic analgesics. For example, the present invention is useful with the various alkaloids of opium such as morphine, morphine salts (such as morphine hydrobromide, morphine hydrochloride, morphine mucate, morphine oleate, morphine N-oxide and morphine sulfate), and morphine analogs such as normorphine, diacetyldihydromorphine, diacetylmorphine hydrochloride, codeine and diacetylmorphine (heroin). Other widely used narcotic analgesics with which the present invention may be used include alphatrodine, methadone, meperidine, leverthanol, hydromorphone, propoxyphene, fentanyl, oxymorphone, anileridine and metophon.

As is well known, continued use of these narcotic analgesics leads to habituation or addiction, and use of one leads to cross-tolerance for the others. However, despite their abuse potential, these narcotic analgesics have therapeutic uses, for example with patients requiring chronic treatment to ease pain.

Even in such therapeutic uses, though, patients develop increasing tolerances to these narcotic analgesics, so that increasingly potent doses are required to achieve relief from pain. Undesirable side effects then tend to develop to the large, chronic doses of the narcotic analgesics.

The agonistic actions and dependence-producing properties of narcotic analgesics can be, and are, studied in various mammalian species besides humans, since practical and governmental considerations frequently require that studies be first done in small rodents and/or monkeys before the analgesic properties of pharmaceuticals are tested with humans. To the present, however, all drugs that have morphine-like properties in mammals other than man have been found to be morphine-like in man, and a variety of analgesic assays have been developed with animals which have gained widespread acceptance for predicting properties in humans.

The present invention is a therapeutic method of using dynorphin with a host tolerant to narcotic analgesics, and more preferably with a mammalian host tolerant to opioid alkaloids. Unless otherwise noted, use of the term "dynorphin" herein includes not only the naturally occurring or synthetically sequenced septadecapeptide, but also those polypeptides having at least the sequence of the ten amino acids of the naturally occurring septadecapeptide. A particularly preferred one dynorphin has the sequence of the thirteen amino acids of the natural product and is referred to as dynorphin-(1–13).

These first thirteen amino acids of dynorphin, or dynorphin-(1–13), have the sequence:

TYR—GLY—GLY—PHE—LEU—ARG—ARG—ILE—ARG—PRO—LYS—LEU—LYS.
1    2    3    4    5    6    7    8    9    10    11    12    13

The N-terminal end of dynorphin-(1–13), contains Leu-enkephalin (those amino acids numbered 1–5), followed by the C-terminal extension (those amino acids numbered 6–13). The inclusion of Leu-enkephalin is believed to be necessary as a biological "homing device" for receptor binding, and the length of the dynorphin's extension beyond Leu-enkephalin is believed to be critical for its potency.

The present invention comprises administering a dose of dynorphin to a host which is tolerant to narcotic analgesics. More particularly, the administering of dynorphin is in conjunction with administering a dose of the narcotic analgesic to which the host is tolerant, wherein the administration of dynorphin is within at least about 30 minutes of the narcotic analgesic dose. Preferably, the administering is by simultaneously administering dynorphin-(1-13) admixed with one or more narcotic analgesics, such as morphine, a morphine analog, or a morphine salt.

The dosage may be determined as follows. A first, or sufficient, dose of the narcotic analgesic is determined which would be sufficient to produce analgesia in the host. However, instead of administering the sufficient dose, a predetermined dose of the narcotic analgesic is administered. This predetermined, or second, dose includes less of the narcotic analgesic than would be sufficient to produce analgesia in the host. The actually administered dose of narcotic analgesic is supplemented with dynorphin, preferably dynorphin-(1-13). The supplementation is preferably sufficient to produce a level of analgesia in the host which is substantially equivalent to the level of analgesia which has been determined were solely the narcotic analgesic to have been administered.

As may be understood, the first or sufficient dose, the lower, second dose, and the supplementing dynorphin dose will vary depending upon the patient's particular level of tolerance to the narcotic analgesic, and will normally be determined by the treating physician.

Although the best mode contemplated for practice of the present invention is in using dynorphin in conjunction with a narcotic analgesic in order to reduce the amount of narcotic analgesic administered per dose, it is also believed that another therapeutic method of using dynorphin is in treating addicts. That is, it is believed that dynorphin is useful in a course of treatment to substantially block withdrawal symptoms.

Presently, many addicts are placed upon a methadone (usually methadone hydrochloride) maintenance program. In conjunction with the administration of methadone, another drug, such as clonidine, is administered in conjunction therewith. However, as is well known methadone is itself addictive, and clonidine is believed to simply mask withdrawal symptoms. As a consequence, patients on such programs are not actually being "cured" of their narcotic addiction.

By contrast, dynorphin-(1-13) has been found to block the withdrawal symptoms of morphine addicted hosts, yet it has been found to be at least 100 times less addictive than morphine. Accordingly, the administering of the present invention may be used to assist in blocking withdrawal symptoms in therapeutic treatments of narcotic addicts being treated for addiction.

Thus, it is believed that administering a dose of dynorphin to a host tolerant to narcotic analgesics will provide a significantly more desirable treatment in treating narcotic addiction.

The following experimental methods, materials and results are described for purposes of illustrating the present invention. However, other aspects, advantages and modifications within the scope of the invention will be apparent to those skilled in the art to which the invention pertains.

Experimental

Male simonesen ICR mice (Gilroy, CA) weighing between 20-25 g were housed for at least one day prior to experimentation, and used within 5 days. Each mouse was used only once.

Analgesia was measured by the tail-flick method of D'Amour and Smith, *J.Pharmac.Exp.Ther.*, 72, pp. 74-79 (1941), incorporated herein by reference, as modified by Tulunay and Takemori, *J.Pharmac.Exp.Ther.*, 190, pp. 395-400 (1974), incorporated herein by reference. For $ED_{50}$ (e.g. effective dose for 50% of the test group) determinations, the animals' responses were made quantal by establishing an endpoint which represented a significant increase in reaction time. The endpoint was an increase in the reaction time of an individual animal of greater than 3 SD (e.g. standard deviation) of the control mean reaction time for all animals used in the assay. The usual control mean reaction time was $3.1 \pm 0.05$ sec. Nonresponding animals were removed from the heat stimulus when reaction times exceeded 10 sec. to avoid the tail damage.

Drugs were injected 30 min prior to testing, unless otherwise indicated. Morphine was injected subcutaneously (s.c.) and $\beta$-endorphin and dynorphin were injected intracerebroventricularly (i.c.v.) in 4 $\mu$l saline.

The animals were separated into two groups. The one group was morphine tolerant (e.g. addicted); the other group was naive (e.g. not addicted). Tolerance was established in each host of the one group by implanting morphine pellets, 75 mg base, subcutaneously by the method of Way et al, *J.Pharmac.Exp.Ther.*, 167, pp. 1-8 (1969), incorporated herein by reference. The pellets were removed 72 hr after implantation, and the mice were tested for morphine tolerance 6 hr later.

At least 30 animals were used from both the morphine tolerant group and from the other, or naive, group to determine each dose-response curve and $ED_{50}$ values of each treatment. The $ED_{50}$ values, their 95% confidence limits and significance of the potency ratio between two $ED_{50}$ values were determined by the method of Litchfield and Wilcoxon, *J.Pharmacol.Exp.Ther*, 96:99-113 (1949), incorporated herein by reference.

The drugs used in these experiments were morphine sulfate (Mallinckrodt Chemical Works, St. Louis, MD) and $\beta$-endorphin (a gift from Dr. N. Ling, Salk Institute, San Diego, CA). Dynorphin and its analogs were from Peninsula Labs. (Belmont, CA).

Examples I and II, below, illustrate the effect of dynorphin-(1-13) in conjunction with morphine and $\beta$-endorphin induced analgesia, respectively, in animals from the morphine tolerant group, when dynorphin-(1-13) was administered in accordance with the inventive method. Example III is described for comparison with Examples I and II.

Although the dynorphin was administered i.c.v. in the Examples I-III, intraveneous (i.v.) administration yielded similar results with comparable doses.

EXAMPLE I

Over 90 morphine tolerant animals were treated with various amounts of morphine sulfate s.c., either alone or in the presence of various amounts of dynorphin-(1-13) i.c.v., and then tested for analgesia. Results of these tests are summarized by the data below, taken from three dose-response curves (each determined from at least 30 animals), one with no dynorphin-(1-13) having been administered, and two with dynorphin-(1–13) having been administered in conjunction with morphine.

| Morphine (mg/kg) | Dynorphin (μg) | Analgesia (%) |
|---|---|---|
| 25 | — | — |
| 60 | — | 40 |
| 80 | — | 90 |
| 15 | 10 | 10 |
| 25 | 10 | 40 |
| 60 | 10 | 85 |
| 15 | 20 | 30 |
| 25 | 20 | 70 |
| 40 | 20 | 100 |

As may be seen from the test results summarized above, dynorphin-(1–13) potentiated the morphine effect. Thus, the $ED_{50}$ of morphine was shifted from about 60 (mg/kg) to about 29 in the presence of 10 μg dynorphin-(1–13), and from about 60 (mg/kg) to about 18 in the presence of 20 μg dynorphin-(1–13).

EXAMPLE II

Over 90 morphine tolerant animals were treated with various amounts of β-endorphin i.c.v., either alone or in the presence of various amounts of dynorphin-(1–13) i.c.v., and then tested for analgesia. Results of these tests are summarized by the data below, taken from three dose-response curves (each determined from at least 30 animals), one with no dynorphin-(1–13) having been administered, and two with dynorphin-(1–13) having been administered in conjunction with morphine.

| β-Endorphin (μg/mouse) | Dynorphin (μg) | Analgesia (%) |
|---|---|---|
| 1 | — | 10 |
| 2 | — | 40 |
| 6 | — | 100 |
| 0.5 | 10 | 10 |
| 1 | 10 | 60 |
| 2 | 10 | 80 |
| 0.25 | 20 | 20 |
| 0.5 | 20 | 40 |
| 1 | 20 | 80 |

As may be seen from the test results summarized above, dynorphin-(1–13) potentiated the β-endorphin effect. Thus, the $ED_{50}$ of β-endorphin was shifted from about 2.25 μg/mouse i.c.v. to about 1.00 and about 0.55 in the presence of 10 and 20 μg dynorphin-(1–13), respectively.

For comparison, Example III, below, illustrates the effect of dynorphin-(1–13) in conjunction with morphine induced analgesia in animals from the naive group.

EXAMPLE III

Over 90 naive animals were treated with morphine sulfate s.c., either alone or in the presence of various amounts of dynorphin-(1–13) i.c.v., and then tested for analgesia. Results of these tests are summarized by the data below taken from three dose-response curves (each determined from at least 30 animals), one with no dynorphin-(1–13) having been administered, and two with dynorphin-(1–13) having been administered in conjunction with morphine.

| Morphine (mg/kg) | Dynorphin (μg) | Analgesia (%) |
|---|---|---|
| 2 | — | 10 |
| 4 | — | 30 |
| 5 | — | 60 |
| 7.5 | — | 80 |
| 3.75 | 10 | 10 |
| 10 | 10 | 60 |
| 15 | 10 | 100 |
| 7.5 | 20 | 10 |
| 10 | 20 | 30 |
| 20 | 20 | 60 |
| 40 | 20 | 100 |

As may be seen from the test results summarized above, dynorphin-(1–13) significantly inhibited the morphine induced analgesia in a dose related manner, and shifted the morphine-response curve to the right. Thus, the $ED_{50}$ of morphine administered s.c. was shifted from about 4.9 mg/kg to about 8.4 and about 14.5 in the presence of 10 and 20 g dynorphin-(1–13), respectively.

A similar effect was observed on analgesia induced by i.c.v. β-endorphin. However, dynorphin-(1–9) up to 40 μg, or -(6–13) up to 80 μg, were inactive in inhibiting morphine induced analgesia in similar experiments.

As may be seen by comparing the data from Example III with Examples I and II, instead of inhibiting a morphine induced analgesia (as occurred in the naive animals of Example III), administering dynorphin to morphine tolerant animals potentiated the morphine effect. This shift in the morphine $ED_{50}$ was not due to dynorphin's own effect, since dynorphin up to 50 μg/mouse still showed no analgesic potency. Similar results occurred with β-endorphin induced analgesia. In both the morphine and β-endorphin cases, the potentiation was dose-related.

The surprising discovery that dynorphin is capable of suppressing withdrawal syndrome in hosts tolerant to narcotic analgesic is illustrated by Example IV, below.

EXAMPLE IV

Morphine pellets (75 mg) were removed 72 hr after implantation in the one, or morphine tolerant, group and mice were tested for jumping response in a 30"×30" cylinder in order to assess spontaneous withdrawal from the narcotic. Mice which jumped were separated and received 4 μl of saline i.c.v. or different doses of dynorphin, and tested 30 min and then 60 min after injection.

Thirty minutes after an injection of saline 90% of the morphine dependent animals tested for withdrawal symptoms were spontaneously jumping, and after sixty minutes 100% were spontaneously jumping. By contrast, dynorphin significantly reduced, or repressed, withdrawal as illustrated by the data below.

| | % spontaneously jumping | |
|---|---|---|
| μg dynorphin-(1–13) | after 30 min. | after 60 min. |
| 10 | 90% | 100% |
| 20 | 60% | 90% |
| 50 | 20% | 70% |

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A therapeutic method of using dynorphin comprising:
administering a dynorphin dose, said dynorphin dose including a polypeptide having at least the sequence TYR-GLY-GLY-PHE-LEU-ARG-ARG-ILE-ARG-PRO, the TYR-GLY-GLY-PHE-LEU portion of said sequence defining an N-terminal end for said polypeptide, the administering being to a host tolerant to a narcotic analgesic.

2. The therapeutic method as in claim 1 wherein:
the administering is in conjunction with administering a dose of the narcotic analgesic to which the host is tolerant.

3. The therapeutic method as in claim 2 wherein:
the administering of said dynorphin dose is within at least about 30 minutes of the administering of said dose of the narcotic analgesic.

4. The therapeutic method as in claim 2 wherein:
said dynorphin dose and said dose of the narcotic analgesic are simultaneously administered.

5. The therapeutic method as in claim 1 wherein:
the dynorphin in said dynorphin dose includes dynorphin-(1-13).

6. The therapeutic method as in claim 2 wherein:
said dose of narcotic analgesic includes an opiate alkaloid.

7. The therapeutic method as in claim 1 or 2 wherein:
the narcotic analgesic is morphine, a morphine analog, or a morphine salt.

8. The therapeutic method as in claim 1 wherein:
said dynorphin dose is administered intraveneously.

9. The therapeutic method as in claim 1 wherein:
said dynorphin dose of the administering is sufficient to retard withdrawal syndrome from occurring in the host.

10. A therapeutic method of producing analgesia in a host tolerant to a narcotic analgesic comprising the steps of:
determining a first dose of said narcotic analgesic, said first dose being sufficient to produce an analgesic level in the host;
administering a predetermined dose of said narcotic analgesic to the host, said second host being lower than said first dose of the determining step; and,
supplementing said second dose with a third dose, said third dose including dynorphin-(1-13), the supplementing being sufficient to produce a level of analgesia in the host which is substantially equivalent to the analgesic level of the determining step.

11. The therapeutic method as in claim 10 wherein:
the supplementing step is within at least about 30 minutes of the administering step.

* * * * *

UNITED STATES PATENT AND TRADEMARK OFFICE
CERTIFICATE OF CORRECTION

PATENT NO. : 4,361,553

DATED : November 30, 1982

INVENTOR(S) : Loh et al.

It is certified that error appears in the above—identified patent and that said Letters Patent is hereby corrected as shown below:

Column 8, line 19, "said second host" should be --said second dose--.

Signed and Sealed this

Twelfth Day of April 1983

[SEAL]

Attest:

GERALD J. MOSSINGHOFF

Attesting Officer

Commissioner of Patents and Trademarks